US011229692B2

(12) United States Patent
Godeaux et al.

(10) Patent No.: US 11,229,692 B2
(45) Date of Patent: *Jan. 25, 2022

(54) METHODS AND COMPOSITIONS FOR INDUCING PROTECTIVE IMMUNITY AGAINST RSV INFECTION

(71) Applicant: Janssen Vaccines & Prevention B.V., Leiden (NL)

(72) Inventors: Olivier Godeaux, Louvain-la-Neuve (BE); Jerald C. Sadoff, Amsterdam (NL); Macaya Julie Douoguih, Reston, VA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 47 days.

This patent is subject to a terminal disclaimer.

(21) Appl. No.: 16/613,206

(22) PCT Filed: May 15, 2018

(86) PCT No.: PCT/EP2018/062604
§ 371 (c)(1),
(2) Date: Nov. 13, 2019

(87) PCT Pub. No.: WO2018/210871
PCT Pub. Date: Nov. 22, 2018

(65) Prior Publication Data
US 2020/0061181 A1 Feb. 27, 2020

Related U.S. Application Data

(60) Provisional application No. 62/507,298, filed on May 17, 2017.

(30) Foreign Application Priority Data

Jun. 13, 2017 (EP) .................................... 17175629

(51) Int. Cl.
| | |
|---|---|
| *A61K 39/12* | (2006.01) |
| *A61P 31/14* | (2006.01) |
| *A61K 35/761* | (2015.01) |
| *C12N 15/86* | (2006.01) |
| *A61K 39/00* | (2006.01) |

(52) U.S. Cl.
CPC ............ *A61K 39/12* (2013.01); *A61K 35/761* (2013.01); *A61P 31/14* (2018.01); *C12N 15/86* (2013.01); *A61K 2039/545* (2013.01); *A61K 2039/55* (2013.01)

(58) Field of Classification Search
None
See application file for complete search history.

(56) References Cited

U.S. PATENT DOCUMENTS

| | | |
|---|---|---|
| 4,235,877 A | 11/1980 | Fullerton |
| 4,372,945 A | 2/1983 | Likhite |
| 4,474,757 A | 10/1984 | Arnon et al. |
| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,083,716 A | 7/2000 | Wilson et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 8,772,256 B2 | 7/2014 | Graham et al. |
| 8,932,607 B2 | 1/2015 | Custers et al. |
| 10,729,757 B2 * | 8/2020 | Langedijk ............... A61P 37/04 |
| 2011/0305727 A1 | 12/2011 | Swanson et al. |
| 2012/0164176 A1 | 6/2012 | Swanson et al. |
| 2012/0315270 A1 | 12/2012 | McLellan et al. |
| 2013/0177573 A1 | 7/2013 | Williamson et al. |

(Continued)

FOREIGN PATENT DOCUMENTS

| | | |
|---|---|---|
| EP | 0853660 A1 | 7/1998 |
| EP | 1230354 | 8/2002 |

(Continued)

OTHER PUBLICATIONS

Farina et al., "Replication-Defective Vector Based on a Chimpanzee Adenovirus", Journal of Virology, vol. 75, No. 23, pp. 11603-11613, Dec. 2001.

Kobinger et al., "Chimpanzee adenovirus vaccine protects against Zaire Ebola Virus", Science Direct, Virology, 346, pp. 394-401, 2006.

Lasaro et al., "New Insights on Adenovirus as Vaccine Vectors", Molecular Therapy, vol. 17, No. 8, pp. 1333-1339, Aug. 2009.

(Continued)

*Primary Examiner* — Shanon A. Foley
*Assistant Examiner* — Myron G Hill
(74) *Attorney, Agent, or Firm* — Ice Miller LLP

(57) ABSTRACT

Compositions, vaccines and methods using adenovirus vectors for inducing protective immunity against a respiratory syncytial virus (RSV) infection are described.

14 Claims, No Drawings

Specification includes a Sequence Listing.

(56) References Cited

U.S. PATENT DOCUMENTS

| | | | |
|---|---|---|---|
| 2014/0073032 A1 | 3/2014 | Custers et al. | |
| 2014/0248314 A1 | 9/2014 | Swanson et al. | |
| 2014/0271699 A1 | 9/2014 | Kwong et al. | |
| 2016/0102123 A1 | 4/2016 | Langedijk et al. | |
| 2016/0145321 A1 | 5/2016 | Wadia et al. | |
| 2016/0145322 A1 | 5/2016 | Wadia et al. | |
| 2016/0176932 A1 | 6/2016 | Langedijk et al. | |
| 2020/0197509 A1* | 6/2020 | Widjojoatmodjo | A61P 31/14 |

FOREIGN PATENT DOCUMENTS

| | | | |
|---|---|---|---|
| WO | 90/03184 A1 | 4/1990 | |
| WO | 90/14837 A1 | 12/1990 | |
| WO | 96/09378 A1 | 3/1996 | |
| WO | 96/11711 A1 | 4/1996 | |
| WO | 98/22588 A2 | 5/1998 | |
| WO | 98/39411 A1 | 9/1998 | |
| WO | 99/12568 A1 | 3/1999 | |
| WO | 99/41416 A2 | 8/1999 | |
| WO | 00/29024 A1 | 5/2000 | |
| WO | 00/32754 A1 | 6/2000 | |
| WO | 200070071 A1 | 11/2000 | |
| WO | 01/66137 A1 | 9/2001 | |
| WO | 2001085984 A1 | 11/2001 | |
| WO | 02/40665 A2 | 5/2002 | |
| WO | 03040178 A1 | 5/2003 | |
| WO | 03/049763 A1 | 6/2003 | |
| WO | 03/061708 A1 | 7/2003 | |
| WO | 03/078592 A2 | 9/2003 | |
| WO | 2003/104467 A1 | 12/2003 | |
| WO | 2004001032 A2 | 12/2003 | |
| WO | 04/004762 A1 | 1/2004 | |
| WO | 04/020971 A2 | 3/2004 | |
| WO | 05/002620 A1 | 1/2005 | |
| WO | 2005071093 A2 | 8/2005 | |
| WO | 2005/080556 A2 | 9/2005 | |
| WO | 06/108707 A1 | 10/2006 | |
| WO | 2007/104792 A2 | 9/2007 | |
| WO | 07/110409 A1 | 10/2007 | |
| WO | 2009/11713 A1 | 1/2009 | |
| WO | 2009/079796 A1 | 7/2009 | |
| WO | 10/060719 A1 | 6/2010 | |
| WO | 2010086189 A2 | 8/2010 | |
| WO | 2010/149743 A2 | 12/2010 | |
| WO | 2010/149745 A1 | 12/2010 | |
| WO | 2011008974 A2 | 1/2011 | |
| WO | 2011/020079 A1 | 2/2011 | |
| WO | 11/045378 A1 | 4/2011 | |
| WO | 11/045381 A1 | 4/2011 | |
| WO | 2011050168 A2 | 4/2011 | |
| WO | 11/098592 A1 | 8/2011 | |
| WO | 2012006596 A2 | 1/2012 | |
| WO | 2012/158613 A1 | 11/2012 | |
| WO | 13/135615 A1 | 9/2013 | |
| WO | 2013/139911 A1 | 9/2013 | |
| WO | 2013/139916 A1 | 9/2013 | |
| WO | WO-2013139911 A1 * | 9/2013 | A61K 39/155 |
| WO | 2014005643 A1 | 1/2014 | |
| WO | 2014160463 A1 | 10/2014 | |
| WO | 2014174018 A1 | 10/2014 | |
| WO | 2014202570 A1 | 12/2014 | |
| WO | 2015013551 A1 | 1/2015 | |
| WO | 2015040002 A1 | 3/2015 | |
| WO | 2017174564 A1 | 10/2017 | |

OTHER PUBLICATIONS

Tatsis et al., "A CD46-binding Chimpanzee Adenovirus Vector as a Vaccine Carrier", American Society of Gene Therapy, vol. 15, No. 3, pp. 608-617, Mar. 2007.
Widjojatomodjo et al., "Recombianant Low-seroprevalent adenoviral vectors Ad26 and Ad35 expressing the respiratory syncytial virus (RSV) fusion protein induce protective immunity against RSV infection in cotton rats", Vaccine, 33, pp. 5406-5414, 2015.
Green et al., "Safety and Immunogenicity of novel respiratory syncytial virus (RSV) vaccines based on the RSV viral proteins F, N and M2-1 encoded by simian adenovirus (PanAd3-RSV) and MVA (MVA-RSV): protocol for an open-label, dose-escalation, single-centre, phase 1 clinical trial in healthy adults", BMJ Open, 13 pages, Oct. 2015.
Grunwald et al., "Novel Vaccine Regimen Elicits Strong Airway Immune Responses and Control of Respiratory Syncytial Virus in Nonhuman Primates", Journal of Virology, vol. 88, No. 8, pp. 3997-4007, Apr. 2014.
Int'l Search Report and Written Opinion dated Sep. 8, 2018 in Int'l Application No. PCT/EP2018/062604.
Comparison to Sequence 16, U.S. Appl. No. 12/517,194; U.S. Pat. No. 8,772,256 (Year: 2014) 4 pages.
International Search Report and Written Opinion issued in PCT/EP2017/062875, dated Aug. 14, 2017, 10 pages.
McLellan et al., "Structural Basis of Respiratory Syncytial Virus Neutralization by Motavizumab," Nature Structural & Molecular Biology, vol. 17, pp. 248-250 (2010).
McLellan et al., "Structure of RSV Fusion Glycoprotein Trimer Bound to a Prefusion-Specific Neutralizing Antibody," Science, vol. 340, pp. 1113-1117 (2013).
McLellan et al., "Structure-Based Design of a Fusion Glycoprotein Vaccine for Respiratory Syncytial Virus," Science, vol. 342, pp. 592-598 (2013).
Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).
Letarov et al., "The Carboxy-Terminal Domain Initiates Trimerization of Bacteriophage T4 Fibritin," Biochemistry (Moscow), vol. 64, No. 7, pp. 817-823 (1999).
Guthe et al., "Very Fast Folding and Association of a Trimerization Domain from Bacteriophage T4 Fibritin," J. Mol. Biol., vol. 337, pp. 905-915 (2004).
"Database UniProt Accession W8CJC7," http://ibis.internal.epo.org/exam/dbfetch.jsp?id=UNIPROT:W8CJC7, Download date: Aug. 12, 2015, 1 page.
Widjaja et al., "Recombinant soluble Respiratory Syncytial Virus F Protein That Lacks Heptad Repeat B, Contains a GCN4 Trimerization Motif and Is Not Cleaved Displays Prefusion-Like Characteristics," PLOS One, 20 pages, Jun. 24, 2015.
Written Opinion dated Oct. 10, 2016 in Int'l Application No. PCT/EP2016/066104.
Int'l Search Report dated Oct. 10, 2016 in Int'l Application No. PCT/EP2016/066104.
Written Opinion dated Oct. 12, 2016 in Int'l Application No. PCT/EP2016/066098.
Int'l Search Report dated Oct. 12, 2016 in Int'l Application No. PCT/EP2016/066098.
Suzuki et al., "An Isoleucine Zipper Peptide Forms a Native-like Triple Stranded Coiled Coil in Solution," Protein Engineering, vol. 11, No. 11, pp. 1051-1055 (1998).
Dames et al., "NMR Structure of a Parallel Homotrimeric Coiled Coil," Nature Structural Biology, vol. 5, No. 8, pp. 687-691 (Aug. 1998).
Calder et al., "Electron Microscopy Of The Human Respiratory Syncytial Virus Fusion Protein And Complexes That It Forms With Monoclonal Antibodies," Virology, vol. 271, pp. 122-131 (2000).
Marbury et al., "A Switch Between Two-, Three-, and Four-Stranded Coiled Coils in GCN4 Leucine Zipper Mutants," Science, vol. 262, pp. 1401-1407.
O'Shea et al., "Evidence That The Leucine Zipper Is A Coiled Coil," Science, vol. 243, pp. 538-542 (Jan. 27, 1989).
Database EMBL, Aug. 28, 1995, Human respiratory syncytial virus, strain RSB89-1734, fusion protein (F) mRNA, complete CDS, XP002729919.
Int'l Search Report and Written Opinion dated Oct. 9, 2014 in Int'l Application No. PCT/EP2014/062655.
Int'l Search Report and Written Opinion dated Aug. 12, 2014 in Int'l Application No. PCT/EP2014/058353.

(56) References Cited

OTHER PUBLICATIONS

Magro et al., "Neutralizing Antibodies Against the Preactive Form of Respiratory Syncytial Virus Protein Offer Unique Possibilities for Clinical Intervention," PNAS, vol. 109, No. 8, pp. 3089-3094 (Feb. 21, 2012).
Yin et al., "Structure of the Parainfluenza Virus 5 F Protein in its Metastable, Prefusion Conformation," Nature, vol. 439, pp. 38-44 (Jan. 5, 2006).
Ngwuta et al, "Prefusion F-Specific Antibodies Determine the Magnitude of RSV Neutralizing Activity in Human Sera," Science Translational Medicine, vol. 7, No. 309, pp. 1-9 (2015).
Int'l Search Report and Written Opinion dated Jun. 12, 2017 in Int'l Application No. PCT/EP2017/057962.
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahamsen et al, "Construction of an Adenovirus Type 7a E1A-Vector," Journal of Virology, vol. 71, No. 11, pp. 8946-8951 (Nov. 1997).
Altaras et al, "Production and Formulation of Adenovirus Vectors," Advances in Biochemical Engineering / Biotechnology, vol. 99, pp. 193-260 (2005).
Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).
Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).
Gao et al, "A Cell Line for High-Yield Production of E1-Deleted Adenovirus Vectors without the Emergence of Replication-Competent Virus," Human Gene Therapy, vol. 11, pp. 213-219 (Jan. 2000).
Goerke et al, "Development of a Novel Adenovirus Purification Process Utilizing Selective Precipitation of Cellular DNA," Biotechnology and Bioengineering, vol. 91, pp. 12-21 (2005).
Havenga et al, "Novel replication-incompetent adenoviral B-group vectors: high vector stability and yield in PER.C6 cells," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).

Krarup et al, "A Highly Stable Prefusion RSV F Vaccine Derived from Structural Analysis of the Fusion Mechanism," Nature Communications, vol. 6, pp. 1-11 (Sep. 2015).
Nan et al, "Development of an Ad7 cosmid system and generation of an Ad7LE1LE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen," Journal of General Virology, vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels, et al., "Replication-Deficient Human Adenovirus Type 35 Vectors for Gene Transfer and Vaccination: Efficient Human Cell Infection and Bypass of Preexisting Adenovirus Immunity.", Journal of Virology, vol. 77, No. 15, pp. 8263-8271, (Aug. 2003).
Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion dated Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
McLellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N67I S215P, RSV CL57-v224, fibritin, SEQ: 74", XP002761983, retrieved from EBI accession No. GSP:BBP75438, Database accession No. BBP75438 sequence.
Neuzil, "Progress toward a Respiratory Syncytial Virus Vaccine", Clinical and Vaccine Immunology, vol. 23, pp. 186-188, 2016.
Bangari et al., "Development of nonhuman adenoviruses as vaccine vectors", Vaccine, 24(7), pp. 849-862, 2006.
Cohen et al., "Chimpanzee adenovirus CV-68 adapted as a gene delivery vector interacts with the coxsackievirus and adenovirus receptor", Journal of General Virology, 83, pp. 151-155, 2002.
Gilman et al., "Rapid profiling of RSV antibody repertoires from the memory B cells of naturally infected adult donors", Science Immunology, 11 pages, Dec. 2016.
Openshaw et al., "Protective and Harmful Immunity to RSV Infection", Annu Rev. Immunol, vol. 35, pp. 501-532, 2017.
Janssen Vaccines & Prevention B.V.: A Study to Evaluate the Safety, Tolerability and Immunogenicity of Two Vaccinations of Ad26. RSV. preF One Year Apart in Adults Aged 60 Years and Older in Stable Health, Oct. 2016, retrieved from the Internet: http://clinicaltrials.gov/ct2/show/record/NCT02926430 (retrived on Nov. 30, 2018.
Int'l Search Report and Written Opinion dated Dec. 17, 2018 in Int'l Application No. PCT/EP2018/074710.
Hotard et al., "Identification of Residues in the Human Respiratory Syncytial Virus Fusion Protein That Modulate Fusion Activity and Pathogenesis", Journal of Virology, Jan. 2015, vol. 89, No. 1, pp. 512-522.

* cited by examiner

METHODS AND COMPOSITIONS FOR INDUCING PROTECTIVE IMMUNITY AGAINST RSV INFECTION

CROSS-REFERENCE TO RELATED APPLICATION

This application is a Section 371 of International Application No. PCT/EP2018/062604, filed May 15, 2018, which was published in the English language on Nov. 22, 2018 under International Publication No. WO 2018/210871 A1, and claims priority under 35 U.S.C. § 119(b) to U.S. Provisional Application No. 62/507,298, filed May 17, 2017 and European Application No. 17175629.9, filed Jun. 13, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_890US", creation date of Nov. 14, 2019, and having a size of 14.9 KB. The sequence listing submitted via EFS-Web is part of the specification and is herein incorporated by reference in its entirety.

FIELD OF THE INVENTION

This invention relates to compositions, vaccines and methods for inducing protective immunity against RSV infection.

BACKGROUND OF THE INVENTION

Respiratory syncytial virus (RSV) is considered to be the most important cause of serious acute respiratory illness in infants and children under 5 years of age. Globally, in 2005, RSV was responsible for an estimated 3.4 million hospitalizations worldwide in children under 5 years of age. Furthermore, 66,000 to 199,000 children younger than 5 years died from RSV-associated acute lower respiratory tract infection (LRTI) in 2005, and 99% of these deaths occurred in developing countries. Nevertheless, the disease burden due to RSV in developed countries is substantial, with RSV infection during childhood linked to the development of wheezing, airway hyperreactivity and asthma. In the United States (US), the infection rate was 68.8% in children younger than 12 months of age and 82.6% during the second year of life. Virtually all children had been infected at least once by 24 months of age, and about one half had experienced 2 infections. In the US, RSV infection in children under 5 years of age is the cause of 57,000 to 175,000 hospitalizations, 500,000 emergency room visits, and approximately 500 deaths each year. In children under 1 year of age, RSV is the most important cause of bronchiolitis, and RSV hospitalization is highest among children under 6 months of age. Major risk factors for severe RSV disease are premature birth and concurrent heart or lung disease; other risk factors include siblings in the household, male sex, and lack of breastfeeding.

Although it is clear that most severe disease occurs during primary infection in infancy, symptomatic upper respiratory tract infections (URTI) occur throughout life. RSV repeatedly re-infects individuals throughout life, and it has been hypothesized that re-infection could be due to the fact that infection with RSV does not induce durable protective immunity or that variations in the virus enable evasion of the immune system.

In addition to children, RSV is an important cause of respiratory infections in the elderly, immunocompromised, and those with underlying chronic cardio-pulmonary conditions. In long-term care facilities, RSV is estimated to infect 5-10% of the residents per year with significant rates of pneumonia (10 to 20%) and death (2 to 5%). In one epidemiology study of RSV burden, it was estimated that 11,000 elderly persons die annually of RSV in the US.

Despite the high disease burden and a strong interest in RSV vaccine development, no licensed vaccine is available for RSV. In the 1960s, a formalin-inactivated RSV (FI-RSV) vaccine was associated with enhanced respiratory disease (ERD) in young children, characterized by an increased rate of RSV-mediated, severe LRTI in the vaccinated individuals compared with the control group. In addition to the FI-RSV vaccine, several live-attenuated and subunit RSV vaccines have been examined in animal models and human studies. Live-attenuated vaccines have been specifically challenged by difficulties related to over- and under-attenuation in infants.

Several vaccine candidates are in development based on a variety of platform technologies including replication incompetent vectors. However, still no licensed vaccines for protection against RSV exists. There thus is an unmet need for safe and effective vaccines that elicit immune responses against RSV viruses.

BRIEF SUMMARY OF THE INVENTION

It is discovered in the present invention that various prime-boost combinations of replication incompetent vectors encoding antigenic RSV protein generate effective immune protection against RSV virus infections in different target populations, in particular in young children.

Accordingly, one general aspect of the present invention relates to a combination vaccine comprising:

(i) a first composition comprising an immunologically effective amount of an adenovirus vector comprising a nucleic acid encoding an antigenic respiratory syncytial virus (RSV) protein; and (ii) a second composition comprising an immunologically effective amount of an adenovirus vector comprising a nucleic acid encoding an antigenic RSV protein, wherein one of the compositions is a priming composition and the other composition is a boosting composition.

In another aspect, the present invention relates to a combination vaccine comprising:

(i) a first composition comprising an immunologically effective amount of an adenovirus vector comprising a nucleic acid encoding an antigenic RSV protein;

(ii) a second composition comprising an immunologically effective amount of an adenovirus vector comprising a nucleic acid encoding an antigenic RSV protein; and (iii) a third composition comprising an immunologically effective amount of an adenovirus vector comprising a nucleic acid encoding an antigenic RSV protein, wherein one of the compositions is a priming composition and the other compositions are boosting compositions.

Another general aspect of the present invention relates to the use of a first composition comprising an immunologically effective amount of an adenovirus vector comprising a nucleic acid encoding an antigenic RSV protein; and a second composition comprising an immunologically effective amount of an adenovirus vector comprising a nucleic acid encoding an antigenic RSV protein, for generating a protective immune response against a RSV virus.

Another aspect of the present invention relates to the use of a first composition comprising an immunologically effective amount of an adenovirus vector comprising a nucleic acid encoding an antigenic RSV protein; and a second composition comprising an immunologically effective amount of an adenovirus vector comprising a nucleic acid encoding an antigenic RSV protein; and a third composition comprising a nucleic acid encoding an antigenic RSV protein, for generating a protective immune response against an RSV virus.

In a preferred embodiment of the invention, the adenovirus vector in the first composition (i) comprises a nucleic acid encoding an antigenic RSV protein having the amino acid sequence of SEQ ID NO: 1 or 2, and the adenovirus vector in the second composition (ii) comprises a nucleic acid encoding an antigenic RSV protein having the amino acid sequence of SEQ ID NO: 1 or 2.

In another preferred embodiment, the adenovirus vector in the third composition comprises a nucleic acid encoding an RSV protein having the amino acid sequence of SEQ ID NO: 1 or 2.

In certain embodiments, the nucleic acid encoding the antigenic RSV protein comprises the nucleic acid sequence of SEQ ID NO: 3 or 4.

It is further contemplated that compositions described herein can be embodied in a kit.

For example, in one embodiment, the present invention can include a kit comprising:

(i) a first composition comprising an immunologically effective amount of an adenovirus vector comprising a nucleic acid encoding an antigenic RSV protein; and (ii) a second composition comprising an immunologically effective amount of an adenovirus vector comprising a nucleic acid encoding an antigenic RSV protein; and, optionally, (iii) a third composition comprising an immunologically effective amount of an adenovirus vector comprising a nucleic acid encoding an antigenic RSV protein.

In a preferred embodiment, the present invention relates to a combination vaccine, a kit or a use as described herein, wherein the adenovirus vector in composition (i) comprises a nucleic acid encoding an RSV F protein having the amino acid sequence of SEQ ID NO: 1 or 2; and wherein the adenovirus vector in composition (ii) comprises a nucleic acid encoding an RSV F protein having the amino acid sequence of SEQ ID NO: 1 or 2.

In another embodiment, the adenovirus vector in composition (iii) comprises a nucleic acid encoding an RSV F protein having the amino acid sequence of SEQ ID NO: 1 or 2.

In a preferred embodiment, the adenovirus vector in composition (i), (ii) and (iii) comprises a nucleic acid encoding an RSV F protein having the amino acid sequence of SEQ ID NO: 1

In certain embodiments, the nucleic acid encoding the antigenic RSV protein comprises the nucleic acid sequence of SEQ ID NO: 3 or 4.

In a preferred embodiment the adenovirus vectors are recombinant Ad26 (rAd26) vectors.

One additional general aspect of the present invention relates to a method of inducing an immune response against an RSV virus in a subject, the method comprising:

(i) administering to the subject a first composition comprising an immunologically effective amount of an adenovirus vector comprising a nucleic acid encoding an antigenic RSV protein; and (ii) administering to the subject a second composition comprising an immunologically effective amount of an adenovirus vector comprising a nucleic acid encoding an antigenic RSV protein; and, optionally, (iii) administering to the subject a third composition comprising an immunologically effective amount of an adenovirus vector comprising a nucleic acid encoding an antigenic RSV protein of an RSV virus.

In a preferred embodiment, the adenovirus vector in the first, second and the optional third composition comprises a nucleic acid encoding an antigenic RSV protein having the amino acid sequence of SEQ ID NO: 1 or 2.

In certain embodiments, the nucleic acid encoding the antigenic RSV protein comprises the nucleic acid sequence of SEQ ID NO: 3 or 4.

In a preferred embodiment, the adenovirus vector in composition (i), (ii) and (iii) comprises a nucleic acid encoding an RSV F protein having the amino acid sequence of SEQ ID NO: 1.

In a preferred embodiment, the adenovirus vectors used in the method of the present invention are recombinant Ad26 vectors.

In certain embodiments, the second composition is administered 1-12 weeks after the first composition, preferably 2-10 weeks, more preferably 4-8 weeks.

In a preferred embodiment, the second composition is administered 4 weeks (i.e. 1 month) or 8 weeks (i.e. 2 months) after the first composition.

In certain embodiment, the third composition is administered 1-12 weeks after the second composition, preferably 2-10 weeks, more preferably 4-8 weeks.

In a preferred embodiment, the third composition, if any, is administered 4 weeks (i.e. 1 month) or 8 weeks (i.e. 2 months) after the first composition.

In a preferred embodiment of the present invention, the method comprises a first (e.g. priming) vaccination with an immunologically effective amount of an Ad26 vector expressing an antigenic RSV protein, followed by a second (e.g. boosting) vaccination with an immunologically effective amount of an Ad26 vector expressing said antigenic RSV protein.

In another embodiment of the present invention, the method comprises a first (e.g. priming) vaccination with an immunologically effective amount of an Ad26 vector expressing an antigenic RSV protein, followed by a second (e.g. boosting) vaccination with an immunologically effective amount of an Ad26 vector expressing an antigenic RSV protein, followed by a third (e.g. boosting) vaccination with an immunologically effective amount of an Ad26 vector, expressing an antigenic RSV protein.

In a preferred embodiment, said RVS antigenic protein is an RSV F protein in a pre-fusion conformation, preferably the RSV F protein comprising the amino acid sequence of SEQ ID NO: 1 or 2, preferably SEQ ID NO: 1.

In certain preferred embodiments, the subject is a child, e.g. an infant or baby, between the age of 0 months and about 24 months. In certain embodiments, the subject is a child between the age of 0 and about 12 months, preferably the subject is a child between the age of about 2 and 6 months.

In a preferred embodiment, the first composition is administered to an infant at birth.

In another preferred embodiment, the first composition is administered to an infant of about 0-8 weeks of age, in particular an infant that is about 1, 2, 3, 4, 5, 6, 7 or 8 weeks old.

In a preferred embodiment, the first composition is administered to an infant of about 2 months of age.

In a preferred embodiment, the first composition is administered to an infant at about 2 months of age and the second composition is administered to said infant at about 3 or 4 months of age.

In another preferred embodiment, the first composition is administered to an infant at about 2 months of age, and the second composition is administered to said infant at about 3 or 4 months of age, and the third composition is administered to said infant at about 4 or 6 months of age.

DETAILED DESCRIPTION OF THE INVENTION

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

The terms "adjuvant" and "immune stimulant" are used interchangeably herein, and are defined as one or more substances that cause stimulation of the immune system. In this context, an adjuvant is used to enhance an immune response to the adenovirus vectors of the invention.

It is discovered in the present invention that homologous prime-boost combinations using recombinant adenovectors, in particular, Ad26 priming followed by Ad26 boosting, are surprisingly effective in generating protective immune responses against RSV viruses in young children. In addition, the vaccines do not result in enhanced respiratory disease and thus are safe.

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the present invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 or 35, more preferably the adenovirus is a human adenovirus of one of the serotypes 26.

An advantage of these serotypes is a low seroprevalence and/or low pre-existing neutralizing antibody titers in the human population. Preparation of recombinant Ad26 vectors is described, for example, in WO 2007/104792 and in Abbink et al., (2007) Virol 81(9): 4654-63, both of which are incorporated by reference herein in their entirety. Exemplary genome sequences of Ad26 are found in GenBank Accession EF 153474 and in SEQ ID NO: 1 of WO 2007/104792. Preparation of recombinant Ad35 vectors is described, for example, in U.S. Pat. No. 7,270,811, in WO 00/70071, and in Vogels et al., (2003) J Virol 77(15): 8263-71, all of which are incorporated by reference herein in their entirety. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2001/085984; Farina et al, 2001, J Virol 75: 11603-13; Cohen et al, 2002, J Gen Virol 83: 151-55; Kobinger et al, 2006, Virology 346: 394-40 I; Tats is et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

In certain embodiments according to the present invention the adenoviral vectors comprise capsid proteins from two rare serotypes: Ad26 and Ad35. In a typical embodiment, the vector is a recombinant Ad26 or Ad35 virus. An "adenovirus capsid protein" refers to a protein on the capsid of an adenovirus (e.g., Ad 26 or Ad 35) that is involved in determining the serotype and/or tropism of a particular adenovirus. Adenoviral capsid proteins typically include the fiber, penton and/or hexon proteins. As used herein a "Ad26 capsid protein" or a "Ad35 capsid protein" can be, for example, a chimeric capsid protein that includes at least a part of an Ad26 or Ad35 capsid protein. In certain embodiments, the capsid protein is an entire capsid protein of Ad26 or of Ad35. In certain embodiments, the hexon, penton and fiber are of Ad26 or of Ad35. Thus, the vectors that can be used in the invention comprise an Ad26 or Ad35 capsid protein (e.g., a fiber, penton or hexon protein). One of skill will recognize that it is not necessary that an entire Ad26 or Ad35 capsid protein be used in the vectors of the invention. Thus, chimeric capsid proteins that include at least a part of an Ad26 or Ad35 capsid protein can be used in the vectors of the invention. The vectors of the invention can also comprise capsid proteins in which the fiber, penton, and hexon proteins are each derived from a different serotype, so long as at least one capsid protein is derived from Ad26 or Ad35. In certain embodiments, the fiber, penton and hexon proteins are each derived from Ad26 or each from Ad35.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of preexisting immunity of the Ad26 and Ad35 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 or from Ad35 (i.e., the vector is Ad26 or Ad35). In some embodiments, the adenovirus is replication deficient, e.g. because it contains a deletion in the E1 region of the genome. For the adenoviruses of the invention, being derived from Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E 1 B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032).

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful for the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention can contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As indicated above, in a preferred embodiment, the adenovectors according to the invention comprise a nucleic acid encoding an antigenic RSV protein. The adenovirus in the first composition and the adenovirus in the second composition and the adenovirus in the third composition can be identical or different. In a preferred embodiment, the adenovirus in the first and second composition, and the adenovirus in the optional third composition are identical.

In certain embodiments, the antigenic RSV protein is an RSV fusion (F) protein. The RSV F protein is conserved between RSV strains making it an attractive vaccine candidate able to elicit broadly neutralizing antibodies. The RSV F protein facilitates infection by fusing the viral and host-cell membranes. In the process of fusion, the F protein refolds irreversibly from a labile pre-fusion conformation to a stable post-fusion conformation. Because of the instability of the RSV F protein, the RSV F protein has the propensity to prematurely refold into its more stable post-fusion conformation. This phenomenon is an intrinsic feature of the protein both in solution and on the surface of the virions. In human sera most RSV neutralizing antibodies are, however, directed against the RSV F in the pre-fusion conformation. In a preferred embodiment of the invention, the antigenic RSV protein therefore is an RSV F protein in the pre-fusion conformation.

In a preferred embodiment of the invention, the adenovirus vector in the first, second and the optional third composition comprises a nucleic acid encoding a RSV fusion (F) protein, preferably a RSV F protein in the pre-fusion conformation, preferably an RSV F protein having the amino acid sequence of SEQ ID NO:1 or 2, preferably SEQ ID NO: 1.

If required, the heterologous gene encoding the RSV proteins can be codon-optimized to ensure proper expression in the treated host (e.g., human). Codon-optimization is a technology widely applied in the art. Typically, the heterologous gene is cloned into the E1 and/or the E3 region of the adenoviral genome.

In certain embodiments, the nucleic acid molecule encoding the RSV pre-fusion F protein comprises the nucleic acid sequence of SEQ ID NO: 3 or 4.

The heterologous RSV gene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

The compositions of the invention can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure. The preparation and use of immunogenic compositions are well known to those of skill in the art. Adjuvants suitable for co-administration in accordance with the present invention should be ones that are potentially safe, well tolerated and effective in people including QS-21, MPL-SE, CpG ODN, Alum, and MF59. Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL', IL-2, IL-4, IL-6, IL-8, IL-10, and IL-12 or encoding nucleic acids therefore. It is also possible to use vector-encoded adjuvant, e.g. by using heterologous nucleic acid that encodes a fusion of the oligomerization domain of C4-binding protein (C4 bp) to the antigen of interest (e.g. Solabomi et al, 2008, Infect Immun 76: 3817-23). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

The present invention further provides a method of priming and boosting an immune response to a RSV virus in a subject using one or more adenoviral vectors for priming and boosting administrations.

According to one general aspect of the present invention, a method of inducing an immune response against a RSV virus in a subject comprises:
(i) administering to the subject a first composition comprising an immunologically effective amount of an adenovirus vector comprising a nucleic acid encoding an antigenic RSV protein;
(ii) administering to the subject a second composition comprising an immunologically effective amount of an adenovirus vector comprising a nucleic acid encoding an antigenic RSV protein, and, optionally
(iii) administering to the subject a third composition comprising an immunologically effective amount of an adenovirus vector comprising a nucleic acid encoding an antigenic RSV protein.

In a preferred embodiment the later step is conducted 1-12 weeks after the previous step, preferably 2-10 weeks, more preferably 4-8 weeks. In a more preferred embodiment the later step is conducted 4 or 8 weeks after the previous step.

In a preferred embodiment, step (ii) is conducted 4 weeks (i.e 1 month) or 8 weeks (i.e. 2 months) after step (i).

In a preferred embodiment, step (iii) is conducted 4 weeks (i.e 1 month) or 8 weeks (i.e. 2 months) after step (ii).

A subject as used herein preferably is a mammal, for instance a rodent, e.g. a mouse, a cotton rat, or a non-human-primate, or a human. Preferably, the subject is a human subject.

In certain preferred embodiments, the subject is a child, for example an infant or baby, between the age of 0 months and about 24 months. In certain embodiments, the subject is a child between the age of 0 and about 12 months, preferably the subject is a child between the age of 0 and 6 months, preferably between about 2 and 6 months.

In a preferred embodiment, the first composition is administered to an infant at birth.

In another preferred embodiment, the first composition is administered to an infant of about 0-8 weeks of age, in particular an infant that is about 1, 2, 3, 4, 5, 6, 7 or 8 weeks old.

In a preferred embodiment, the first composition is administered to an infant of about 2 months of age.

In a preferred embodiment, the first composition is administered to an infant at about 2 months of age and the second composition is administered to said infant at about 3 or 4 months of age.

In another preferred embodiment, the first composition is administered to an infant at about 2 months of age, and the second composition is administered to said infant at about 3 or 4 months of age, and the third composition is administered to said infant at about 4 or 6 months of age.

The subject may be seronegative or seropositive. Seropositive subjects typically show a significant level of serum antibodies, or other immunologic marker in the serum, indicating previous exposure to RSV. In certain embodiments, the subject is a seronegative subject, i.e. showing no significant level of serum antibodies, or other immunologic marker in the serum, that would indicate previous exposure to RSV.

In a preferred embodiment according to this method, an Ad26 vector is used for the priming followed by one or more boosting steps with an Ad26 vector. Preferably, the boosting composition is administered 1-12 weeks after priming, more preferably 4 or 8 weeks after priming. In a preferred embodiment, the boosting composition is administered 8 weeks after priming. In another preferred embodiment, the boosting composition is administered 4 weeks after priming.

For administering to humans, the invention may employ compositions comprising the adenovirus vectors together with a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified adenovector preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g pH 5.0 to 7.5. The adenovector typically is in a solution having a suitable pharmaceutically acceptable buffer, and the solution may also contain a salt. Optionally stabilizing agent may be present, such as albumin. In certain embodiments, detergent is added. In certain embodiments, the compositions may be formulated into an injectable preparation. For instance, adenovirus may be stored in the buffer that is also used for the Adenovirus World Standard (Hoganson et al, Development of a stable adenoviral vector formulation, Bioprocessing March 2002, p. 43-48): 20 mM Tris pH 8, 25 mM NaCl, 2.5% glycerol. Another useful formulation buffer suitable for administration to humans is 20 mM Tris, 2 mM MgCl2, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can for instance be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

In another preferred embodiment, use is made of an adenovirus formulation as described in WO2015/040002. Thus, in a preferred embodiment of the inventions, the first, second and optional third composition comprising the adenovirus vector comprising a nucleic acid encoding an antigenic RSV protein comprise: a recombinant adenovirus; a citrate buffer, wherein the citrate concentration is ranging between about 5 mM and 30 mM; hydroxypropyl-beta-cyclodextrin (HBCD), wherein the concentration of HBCD is ranging between about 1% (w/w) and 10% (w/w); a salt, e.g. sodium chloride in a concentration between about 20 mM and about 200 mM; and non-ionic detergent, e.g. Polysorbate-80 in a concentration ranging from about 0.005% (w/w) to about 0.5% (w/w); wherein said formulation has a pH ranging between 5.5 and 6.5.

In certain embodiments, the compositions have a pH ranging between about 5.7 and 6.3, and comprise citrate at a concentration ranging between about 5 and 30 mM; HBCD at a concentration ranging between 1% (w/w) and 10% (w/w); NaCl at a concentration ranging between 20 mM and 200 mM; Polysorbate-80 at a concentration ranging between about 0.01% (w/w) and 0.05% (w/w).

In certain embodiments, the compositions comprise citrate at a concentration of about 15 mM; HBCD at a concentration of about 5% (w/w); NaCl at a concentration of about 75 mM, and Polysorbate-80 at a concentration of about 0.03% (w/w).

In certain embodiments, the compositions further comprise ethanol, wherein the ethanol concentration is ranging between about 0.1% (w/w) to 1% (w/w).

In a preferred embodiment, the compositions comprise citrate at a concentration of about 15 mM; HBCD at a concentration of about 5% (w/w); NaCl at a concentration of about 75 mM, Polysorbate-80 at a concentration of about 0.03% (w/w) and ethanol at a concentration of about 0.4% (w/w).

Administration of the immunogenic compositions comprising the vectors is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the adenovirus vector. An alternative is the use of a needleless injection device to administer the composition (using, e.g., Biojector™) or a freeze-dried powder containing the vaccine.

The immunogenic compositions containing the adenovirus vectors are administered to a subject, giving rise to an anti-RSV virus immune response in the subject. An amount of a composition sufficient to induce a detectable immune response is defined to be an "immunologically effective dose." As shown below, the immunogenic compositions of the invention induce a humoral as well as a cell-mediated immune response. In a typical embodiment the immune response is a protective immune response.

Following production of adenovirus vectors and optional formulation of such particles into immunogenic compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the adenovirus vectors.

In one exemplary regimen, the adenovirus vector is administered (e.g., intramuscularly) in a volume ranging between about 100 µl to about 10 ml containing concentrations of about $10^4$ to $10^{12}$ virus particles/ml. Preferably, the adenovirus vector is administered in a volume ranging between 0.25 and 1.0 ml. More preferably the adenovirus vector is administered in a volume of 0.5 ml.

Typically, the adenovirus is administered in an amount of about $10^9$ to about $10^{12}$ viral particles (vp) to a human subject during one administration, more typically in an amount of about $10^{10}$ to about $10^{12}$ vp. The human adenovirus vector can be administered in a concentration of about $10^7$ vp/ml, $10^8$ vp/ml, $10^9$ vp/ml, $10^{10}$ vp/ml $5\times10^{10}$ vp/ml, $10^{11}$ vp/ml, or $10^{12}$ vp/ml. In a preferred embodiment, the adenovirus vector is administered in an amount of about $1\times10^{11}$ vp. In another preferred embodiment, the adenovirus vector is administered in an amount of about $5\times10^{10}$ vp.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

EXAMPLES

The following examples are provided to illustrate, but not to limit the claimed invention.

Example 1

A clinical study will be performed in humans for evaluating the safety, tolerability and immunogenicity of Ad26.RSV.preF in Adults 18 to 50 Years of Age, RSV-seropositive and RSV-seronegative Toddlers 12 to 24 Months of Age.

The adenovirus-vectored vaccine candidate assessed in this study is:

Ad26.RSV.preF, a replication-incompetent adenovirus serotype 26 (Ad26) containing a deoxyribonucleic acid transgene that encodes for the pre-fusion conformation-stabilized F protein (pre-F) derived from the respiratory syncytial virus (RSV) A2 strain having an amino acid sequence of SEQ ID NO: 1.

Safety will be assessed by collection of solicited local and systemic adverse events, unsolicited adverse events and serious adverse events, and by physical examination. In addition, standard chemistry, hematologic (including coagulation parameters) and urinalysis parameters may be assessed at multiple time points. Immunogenicity will be assessed using the immunologic assays summarized in Tables 1 and 2.

TABLE 1

Summary of Immunogenicity Assays (Humoral)

| Assay | Purpose |
| --- | --- |
| Secondary endpoints | |
| RSV neutralization A | Analysis of neutralizing antibodies to the A strain |
| F-protein antibody (ELISA; pre- and/or post-fusion) | Analysis of antibodies binding to RSV F protein in post-fusion and/or pre-fusion form |

TABLE 1-continued

Summary of Immunogenicity Assays (Humoral)

| Assay | Purpose |
|---|---|
| Exploratory endpoints | |
| RSV strain cross-neutralization | Analysis of cross-neutralizing antibodies to B and/or a different A strain(s) |
| F-protein antibody specificity characterization | Pre- and post-F specificity by binding or functional assays as ELISA, and/or competition ELISA. Adsorption of serum or plasma with pre-F and post-F protein before any antibody assay, epitope mapping, functional VNA |
| Adenovirus neutralization assay | Analysis of neutralizing antibodies to adenovirus |
| Functional and molecular antibody characterization | Analysis of antibody characteristics including ADCC, ADCP, avidity, Fc characteristics, Ig isotype, functional VNA and protective antibody assessments |

ADCC = antibody-dependent cell-mediated cytotoxicity;
ADCP = antibody-dependent cellular phagocytosis;
ELISA = enzyme-linked immunosorbent assay;
F = fusion;
Ig = immunoglobulin;
RSV = respiratory syncytial virus;
VNA = virus neutralizing antibody

TABLE 2

Summary of Immunogenicity Assays (Cellular)

| Assay | Purpose |
|---|---|
| Secondary endpoints | |
| Flow cytometry (ICS)* | Analysis of T-cell responses to RSV F-protein peptides for Th1/Th2 subtyping |
| Exploratory endpoints | |
| IFNγ ELISpot | T-cell IFNγ responses to RSV F-protein peptides |
| ICS | Analysis of T-cell responses to RSV F-protein peptide-stimulated PBMCs (including but not limited to, CD4/CD8, IL2, INFγ, TNFα, activation markers and memory) |
| Cytokine analysis | Analysis of secreted cytokines in RSV F peptide-stimulated PBMC supernatant, including, but not limited to, measurement of Th1/Th2 cytokine balance |

ELISpot = enzyme-linked immunospot;

F = fusion;

ICS = intracellular cytokine staining;

IFNγ = interferon gamma;

IL = interleukin;

PBMC = peripheral blood mononuclear cell;

Th = T-helper (cell);

RSV = respiratory syncytial virus;

TNFα = tumor necrosis factor alpha

*Cytokine analysis for Th1/Th2 profiling will be done to replace samples in cases where no ICS data can be generated or no data are available

SEQUENCES

Amino acid sequences of the RSV pre-fusion F proteins encoded by the nucleic acid molecules of the invention SEQ ID NO: 1: RSV preF2.2 amino acid sequence:
MELLILKANAITTILTAVTFCFASGQNITEEFYQSTCSAVSKGYLSALRT
GWYTSVITIELSNIKEIKCNGTDAKVKLIKQELDKYKNAVTELQLLMQST
PATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSIPNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSNEFDASISQVNEKIN
QSLAFIRKSDELLHNVNAVKSTTNIMITTIIIVIIVILLSLIAVGLLLYC
KARSTPVTLSKDQLSGINNIAFSN SEQ ID NO: 2: RSV preF2.1 amino acid sequence:
MELLILKANAITTILTAVTFCFASGQNITEEFYQSTCSAVSKGYLGALRT
GWYTSVITIELSNIKEIKCNGTDAKVKLIKQELDKYKNAVTELQLLMQST
PATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYID
KQLLPIVNKQSCSIPNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINFYDPLVFPSDEFDASISQVNEKIN
QSLAFIRKSDELLHNVNAVKSTTNIMITTIIIVIIVILLSLIAVGLLLYC
KARSTPVTLSKDQLSGINNIAFSN Nucleotide sequence of preferred nucleic acid molecules of the invention SEQ ID NO: 3: codon optimized nucleic acid encoding the RSV F pre-F2.2 pre-fusion protein
ATGGAGCTGCTGATCCTGAAGGCCAACGCCATCACCACCATCCTGACCGC
CGTGACCTTCTGCTTCGCCAGCGGCCAGAACATCACCGAGGAGTTCTACC
AGAGCACCTGCAGCGCCGTGAGCAAGGGCTACCTGAGCGCCCTGAGAACC
GGCTGGTACACCAGCGTGATCACCATCGAGCTGAGCAACATCAAGGAGAT
CAAGTGCAACGGCACCGACGCCAAGGTGAAGCTGATCAAGCAGGAGCTGG
ACAAGTACAAGAACGCCGTGACCGAGCTGCAGCTGCTGATGCAGAGCACC
CCCGCCACCAACAACAGAGCCAGAAGAGAGCTGCCCAGATTCATGAACTA
CACCCTGAACAACGCCAAGAAGACCAACGTGACCCTGAGCAAGAAGAGAA
AGAGAAGATTCCTGGGCTTCCTGCTGGGCGTGGGCAGCGCCATCGCCAGC
GGCGTGGCCGTGAGCAAGGTGCTGCACCTGGAGGGCGAGGTGAACAAGAT
CAAGAGCGCCCTGCTGAGCACCAACAAGGCCGTGGTGAGCCTGAGCAACG
GCGTGAGCGTGCTGACCAGCAAGGTGCTGGACCTGAAGAACTACATCGAC
AAGCAGCTGCTGCCCATCGTGAACAAGCAGAGCTGCAGCATCCCCAACAT
CGAGACCGTGATCGAGTTCCAGCAGAAGAACAACAGACTGCTGGAGATCA
CCAGAGAGTTCAGCGTGAACGCCGGCGTGACCACCCCCGTGAGCACCTAC
ATGCTGACCAACAGCGAGCTGCTGAGCCTGATCAACGACATGCCCATCAC
CAACGACCAGAAGAAGCTGATGAGCAACAACGTGCAGATCGTGAGACAGC
AGAGCTACAGCATCATGAGCATCATCAAGGAGGAGGTGCTGGCCTACGTG
GTGCAGCTGCCCCTGTACGGCGTGATCGACACCCCCTGCTGGAAGCTGCA
CACCAGCCCCCTGTGCACCACCAACACCAAGGAGGGCAGCAACATCTGCC
TGACCAGAACCGACAGAGGCTGGTACTGCGACAACGCCGGCAGCGTGAGC
TTCTTCCCCCAGGCCGAGACCTGCAAGGTGCAGAGCAACAGAGTGTTCTG
CGACACCATGAACAGCCTGACCCTGCCCAGCGAGGTGAACCTGTGCAACG
TGGACATCTTCAACCCCAAGTACGACTGCAAGATCATGACCAGCAAGACC
GACGTGAGCAGCAGCGTGATCACCAGCCTGGGCGCCATCGTGAGCTGCTA
CGGCAAGACCAAGTGCACCGCCAGCAACAAGAACAGAGGCATCATCAAGA
CCTTCAGCAACGGCTGCGACTACGTGAGCAACAAGGGCGTGGACACCGTG
AGCGTGGGCAACACCCTGTACTACGTGAACAAGCAGGAGGGCAAGAGCCT
GTACGTGAAGGGCGAGCCCATCATCAACTTCTACGACCCCCTGGTGTTCC
CCAGCAACGAGTTCGACGCCAGCATCAGCCAGGTGAACGAGAAGATCAAC
CAGAGCCTGGCCTTCATCAGAAAGAGCGACGAGCTGCTGCACAACGTGAA
CGCCGTGAAGAGCACCACCAACATCATGATCACCACCATCATCATCGTGA
TCATCGTGATCCTGCTGAGCCTGATCGCCGTGGGCCTGCTGCTGTACTGC
AAGGCCAGAAGCACCCCCGTGACCCTGAGCAAGGACCAGCTGAGCGGCAT
CAACAACATCGCCTTCAGCAACTGA SEQ ID NO: 4: codon optimized nucleic acid encoding the RSV F pre-F2.1 pre-fusion protein
ATGGAGCTGCTGATCCTGAAGGCCAACGCCATCACCACCATCCTGACCGC
CGTGACCTTCTGCTTCGCCAGCGGCCAGAACATCACCGAGGAGTTCTACC
AGAGCACCTGCAGCGCCGTGAGCAAGGGCTACCTGGGCGCCCTGAGAACC
GGCTGGTACACCAGCGTGATCACCATCGAGCTGAGCAACATCAAGGAGAT
CAAGTGCAACGGCACCGACGCCAAGGTGAAGCTGATCAAGCAGGAGCTGG
ACAAGTACAAGAACGCCGTGACCGAGCTGCAGCTGCTGATGCAGAGCACC
CCCGCCACCAACAACAGAGCCAGAAGAGAGCTGCCCAGATTCATGAACTA
CACCCTGAACAACGCCAAGAAGACCAACGTGACCCTGAGCAAGAAGAGAA
AGAGAAGATTCCTGGGCTTCCTGCTGGGCGTGGGCAGCGCCATCGCCAGC
GGCGTGGCCGTGAGCAAGGTGCTGCACCTGGAGGGCGAGGTGAACAAGAT
CAAGAGCGCCCTGCTGAGCACCAACAAGGCCGTGGTGAGCCTGAGCAACG
GCGTGAGCGTGCTGACCAGCAAGGTGCTGGACCTGAAGAACTACATCGAC
AAGCAGCTGCTGCCCATCGTGAACAAGCAGAGCTGCAGCATCCCCAACAT
CGAGACCGTGATCGAGTTCCAGCAGAAGAACAACAGACTGCTGGAGATCA
CCAGAGAGTTCAGCGTGAACGCCGGCGTGACCACCCCCGTGAGCACCTAC
ATGCTGACCAACAGCGAGCTGCTGAGCCTGATCAACGACATGCCCATCAC
CAACGACCAGAAGAAGCTGATGAGCAACAACGTGCAGATCGTGAGACAGC
AGAGCTACAGCATCATGAGCATCATCAAGGAGGAGGTGCTGGCCTACGTG
GTGCAGCTGCCCCTGTACGGCGTGATCGACACCCCCTGCTGGAAGCTGCA
CACCAGCCCCCTGTGCACCACCAACACCAAGGAGGGCAGCAACATCTGCC
TGACCAGAACCGACAGAGGCTGGTACTGCGACAACGCCGGCAGCGTGAGC
TTCTTCCCCCAGGCCGAGACCTGCAAGGTGCAGAGCAACAGAGTGTTCTG
CGACACCATGAACAGCCTGACCCTGCCCAGCGAGGTGAACCTGTGCAACG
TGGACATCTTCAACCCCAAGTACGACTGCAAGATCATGACCAGCAAGACC
GACGTGAGCAGCAGCGTGATCACCAGCCTGGGCGCCATCGTGAGCTGCTA
CGGCAAGACCAAGTGCACCGCCAGCAACAAGAACAGAGGCATCATCAAGA
CCTTCAGCAACGGCTGCGACTACGTGAGCAACAAGGGCGTGGACACCGTG
AGCGTGGGCAACACCCTGTACTACGTGAACAAGCAGGAGGGCAAGAGCCT
GTACGTGAAGGGCGAGCCCATCATCAACTTCTACGACCCCCTGGTGTTCC
CCAGCGACGAGTTCGACGCCAGCATCAGCCAGGTGAACGAGAAGATCAAC
CAGAGCCTGGCCTTCATCAGAAAGAGCGACGAGCTGCTGCACAACGTGAA
CGCCGTGAAGAGCACCACCAACATCATGATCACCACCATCATCATCGTGA
TCATCGTGATCCTGCTGAGCCTGATCGCCGTGGGCCTGCTGCTGTACTGC
AAGGCCAGAAGCACCCCCGTGACCCTGAGCAAGGACCAGCTGAGCGGCAT
CAACAACATCGCCTTCAGCAACTGA

The invention claimed is:

1. A vaccine combination comprising:
(i) a first composition comprising an immunologically effective amount of a first adenovirus vector comprising a nucleic acid encoding an antigenic respiratory syncytial virus (RSV) protein having the amino acid sequence of SEQ ID NO: 1 or 2; and
(ii) a second composition comprising an immunologically effective amount of a second adenovirus vector comprising a nucleic acid encoding an antigenic RSV protein having the amino acid sequence of SEQ ID NO: 1 or 2,
wherein one of the compositions is a priming composition and the other composition is a boosting composition.

2. The vaccine combination according to claim 1, further comprising:
(iii) a third composition comprising an immunologically effective amount of a third adenovirus vector comprising a nucleic acid encoding an antigenic RSV protein.

3. The vaccine combination according to claim 2, wherein the third adenovirus vector comprises a nucleic acid encoding an RSV F protein having the amino acid sequence of SEQ ID NO: 1 or 2.

4. The vaccine combination according to claim 1, wherein the adenovirus vectors are recombinant Ad26 vectors.

5. A method of inducing an immune response against RSV in a subject, the method comprising:

(i) administering to the subject a first composition comprising an immunologically effective amount of a first adenovirus vector comprising a nucleic acid encoding an antigenic RSV protein; and
(ii) administering to the subject a second composition comprising an immunologically effective amount of a second adenovirus vector comprising a nucleic acid encoding an antigenic RSV protein,
wherein the adenovirus vector in the first composition (i) comprises a nucleic acid encoding an RSV protein having the amino acid sequence of SEQ ID NO: 1 or 2, and the adenovirus vector in the second composition (ii) comprises a nucleic acid encoding an RSV protein having the amino acid sequence of SEQ ID NO: 1 or 2.

6. The method according to claim 5, further comprising:
(iii) administering to the subject a third composition comprising an immunologically effective amount of an adenovirus vector comprising a nucleic acid encoding an antigenic RSV protein.

7. The method according to claim 6, wherein the adenovirus vector in the third composition comprises a nucleic acid encoding an RSV F protein having the amino acid sequence of SEQ ID NO: 1 or 2.

8. The method according to claim 5, wherein the adenovirus vectors are Ad26 vectors.

9. The method according to claim 5, wherein step (i) and step (ii) of the method are conducted 1-12 weeks apart.

10. The method according to claim 6, wherein step (ii) and step (iii) of the method are conducted 1-12 weeks apart.

11. The method according to claim 5, wherein the subject is a child of about 0 to 24 months of age.

12. The method according to claim 5, wherein step (i) is conducted in an infant of about 0-2 months of age.

13. The method according to claim 5, wherein the first composition is administered to an infant at about 2 months of age and the second composition is administered to said infant at about 3 or 4 months of age.

14. The method according to claim 6, wherein the first composition is administered to an infant at about 2 months of age and the second composition is administered to said infant at about 3 or 4 months of age and the third composition is administered to said infant at about 4 or 6 months of age.

* * * * *

SEQUENCE LISTING

<160> NUMBER OF SEQ ID NOS: 4

<210> SEQ ID NO 1
<211> LENGTH: 574
<212> TYPE: PRT
<213> ORGANISM: Artificial Sequence
<220> FEATURE:
<223> OTHER INFORMATION: RSV preF2.2

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe

```
            20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
            50                  55                  60
Lys Glu Ile Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
            115                 120                 125
Leu Ser Lys Lys Arg Lys Arg Arg Phe Leu Gly Phe Leu Leu Gly Val
            130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
            195                 200                 205
Lys Gln Ser Cys Ser Ile Pro Asn Ile Glu Thr Val Ile Glu Phe Gln
            210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
            290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
```

```
Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Val Lys Ser Thr Thr Asn Ile Met Ile Thr
                515                 520                 525

Thr Ile Ile Ile Val Ile Ile Val Ile Leu Leu Ser Leu Ile Ala Val
                530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Artificial Sequence
<220> FEATURE:
<223> OTHER INFORMATION: RSV preF2.1

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
                35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Pro Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 3
<211> LENGTH: 1725
<212> TYPE: DNA
<213> ORGANISM: Artificial Sequence
<220> FEATURE:
<223> OTHER INFORMATION: codon optimized nucleic acid encoding the RSV F
      pre-F2.2

<400> SEQUENCE: 3
atggagctgc tgatcctgaa ggccaacgcc atcaccacca tcctgaccgc cgtgaccttc    60
tgcttcgcca gcggccagaa catcaccgag gagttctacc agagcacctg cagcgccgtg   120

```
agcaagggct acctgagcgc cctgagaacc ggctggtaca ccagcgtgat caccatcgag      180
ctgagcaaca tcaaggagat caagtgcaac ggcaccgacg ccaaggtgaa gctgatcaag      240
caggagctgg acaagtacaa gaacgccgtg accgagctgc agctgctgat gcagagcacc      300
cccgccacca caacagagc cagaagagag ctgcccagat tcatgaacta caccctgaac      360
aacgccaaga gaccaacgt gaccctgagc aagaagagaa agagaagatt cctgggcttc      420
ctgctgggcg tgggcagcgc catcgccagc ggcgtggccg tgagcaaggt gctgcacctg      480
gagggcgagg tgaacaagat caagagcgcc ctgctgagca ccaacaaggc cgtggtgagc      540
ctgagcaacg gcgtgagcgt gctgaccagc aaggtgctgg acctgaagaa ctacatcgac      600
aagcagctgc tgcccatcgt gaacaagcag agctgcagca tccccaacat cgagaccgtg      660
atcgagttcc agcagaagaa caacagactg ctggagatca ccagagagtt cagcgtgaac      720
gccggcgtga ccaccccgt gagcacctac atgctgacca cagcgagct gctgagcctg      780 atcaacgaca tgcccatcac caacgaccag aagaagctga tgagcaacaa cgtgcagatc      840
gtgagacagc agagctacag catcatgagc atcatcaagg aggaggtgct ggcctacgtg      900
gtgcagctgc cctgtacgg cgtgatcgac acccctgct ggaagctgca caccagcccc      960
ctgtgcacca ccaacaccaa ggagggcagc aacatctgcc tgaccagaac cgacagaggc     1020
tggtactgcg acaacgccgg cagcgtgagc ttcttccccc aggccgagac cctgcaaggtg     1080 cagagcaaca gagtgttctg cgacaccatg aacagcctga cctgcccag cgaggtgaac     1140 ctgtgcaacg tggacatctt caaccccaag tacgactgca agatcatgac cagcaagacc     1200
gacgtgagca gcagcgtgat caccagcctg ggcgccatcg tgagctgcta cggcaagacc     1260
aagtgcaccg ccagcaacaa gaacagaggc atcatcaaga ccttcagcaa cggctgcgac     1320
tacgtgagca acaagggcgt ggacaccgtg agcgtgggca acacccctgta ctacgtgaac     1380 aagcaggagg gcaagagcct gtacgtgaag ggcgagccca tcatcaactt ctacgacccc     1440
ctggtgttcc ccagcaacga gttcgacgcc agcatcagcc aggtgaacga gaagatcaac     1500
cagagcctgg ccttcatcag aaagagcgac gagctgctgc acaacgtgaa cgccgtgaag     1560
agcaccacca acatcatgat caccaccatc atcatcgtga tcatcgtgat cctgctgagc     1620
ctgatcgccg tgggcctgct gctgtactgc aaggccagaa gcacccccgt gaccctgagc     1680
aaggaccagc tgagcggcat caacaacatc gccttcagca actga                    1725
```

<210> SEQ ID NO 4
<211> LENGTH: 1725
<212> TYPE: DNA
<213> ORGANISM: Artificial Sequence
<220> FEATURE:
<223> OTHER INFORMATION: codon optimized nucleic acid encoding the RSV F
    pre-F2.1 pre-fusion protein

<400> SEQUENCE: 4

```
atggagctgc tgatcctgaa ggccaacgcc atcaccacca tcctgaccgc cgtgaccttc       60
tgcttcgcca gcggccagaa catcaccgag gagttctacc agagcacctg cagcgccgtg      120
agcaagggct acctgggcgc cctgagaacc ggctggtaca ccagcgtgat caccatcgag      180
ctgagcaaca tcaaggagat caagtgcaac ggcaccgacg ccaaggtgaa gctgatcaag      240
caggagctgg acaagtacaa gaacgccgtg accgagctgc agctgctgat gcagagcacc      300
cccgccacca caacagagc cagaagagag ctgcccagat tcatgaacta caccctgaac      360
aacgccaaga gaccaacgt gaccctgagc aagaagagaa agagaagatt cctgggcttc      420
```

```
                                                                  -continued ctgctgggcg tgggcagcgc catcgccagc ggcgtggccg tgagcaaggt gctgcacctg    480
gagggcgagg tgaacaagat caagagcgcc ctgctgagca ccaacaaggc cgtggtgagc    540
ctgagcaacg gcgtgagcgt gctgaccagc aaggtgctgg acctgaagaa ctacatcgac    600
aagcagctgc tgcccatcgt gaacaagcag agctgcagca tccccaacat cgagaccgtg    660
atcgagttcc agcagaagaa caacagactg ctggagatca ccagagagtt cagcgtgaac    720
gccggcgtga ccaccccgt gagcacctac atgctgacca cagcgagct gctgagcctg      780 atcaacgaca tgcccatcac caacgaccag aagaagctga tgagcaacaa cgtgcagatc    840
gtgagacagc agagctacag catcatgagc atcatcaagg aggaggtgct ggcctacgtg    900
gtgcagctgc ccctgtacgg cgtgatcgac acccctgct ggaagctgca caccagcccc     960
ctgtgcacca ccaacaccaa ggagggcagc aacatctgcc tgaccagaac cgacagaggc   1020
tggtactgcg acaacgccgg cagcgtgagc ttcttccccc aggccgagac ctgcaaggtg   1080
cagagcaaca gagtgttctg cgacaccatg aacagcctga ccctgcccag cgaggtgaac   1140
ctgtgcaacg tggacatctt caaccccaag tacgactgca agatcatgac cagcaagacc   1200
gacgtgagca gcagcgtgat caccagcctg ggcgccatcg tgagctgcta cggcaagacc   1260
aagtgcaccg ccagcaacaa gaacagaggc atcatcaaga ccttcagcaa cggctgcgac   1320
tacgtgagca acaagggcgt ggacaccgtg agcgtgggca caccctgta ctacgtgaac    1380 aagcaggagg gcaagagcct gtacgtgaag ggcgagccca tcatcaactt ctacgacccc   1440
ctggtgttcc ccagcgacga gttcgacgcc agcatcagcc aggtgaacga gaagatcaac   1500
cagagcctgg ccttcatcag aaagagcgac gagctgctgc acaacgtgaa cgccgtgaag   1560
agcaccacca acatcatgat caccaccatc atcatcgtga tcatcgtgat cctgctgagc   1620
ctgatcgccg tgggcctgct gctgtactgc aaggccagaa gcacccccgt gacccctgagc  1680 aaggaccagc tgagcggcat caacaacatc gccttcagca actga                   1725
```